United States Patent
Sathitsuksanoh et al.

(10) Patent No.: US 10,112,916 B2
(45) Date of Patent: Oct. 30, 2018

(54) HMF PRODUCTION FROM GLUCOSE IN IONIC LIQUID MEDIA

(71) Applicants: The Regents of The University of California, Oakland, CA (US); Sandia Corporation, Albuquerque, NM (US); Virdia Inc., Danville, VA (US)

(72) Inventors: Noppadon Sathitsuksanoh, Berkeley, CA (US); Philip Travisano, III, Danville, VA (US); Anthe George, San Francisco, CA (US); Robert Jansen, Collinsville, IL (US); Blake A. Simmons, San Francisco, CA (US); Seema Singh, Fremont, CA (US)

(73) Assignees: The Regents of the University of California, Oakland, CA (US); Virdia Inc., Danville, VA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 14/970,965

(22) Filed: Dec. 16, 2015

(65) Prior Publication Data
US 2016/0176838 A1    Jun. 23, 2016

Related U.S. Application Data

(60) Provisional application No. 62/096,458, filed on Dec. 23, 2014.

(51) Int. Cl.
| | | |
|---|---|---|
| C07D 307/28 | (2006.01) | |
| C12P 19/24 | (2006.01) | |
| C12P 19/02 | (2006.01) | |

(52) U.S. Cl.
CPC ............ *C07D 307/28* (2013.01); *C12P 19/02* (2013.01); *C12P 19/24* (2013.01)

(58) Field of Classification Search
None
See application file for complete search history.

(56) References Cited

U.S. PATENT DOCUMENTS

| | | | |
|---|---|---|---|
| 3,684,574 A | | 8/1972 | Katz et al. |
| 3,868,304 A | * | 2/1975 | Messing ............... C12N 11/14 435/176 |
| 4,463,093 A | | 7/1984 | Horwath et al. |
| 7,939,681 B2 | * | 5/2011 | Zhao .................... C07D 307/46 549/488 |
| 8,236,973 B2 | | 8/2012 | Liu et al. |
| 8,637,660 B2 | | 1/2014 | Fanselow et al. |
| 2010/0081833 A1 | * | 4/2010 | Gruter .................. C10L 1/1857 549/499 |
| 2011/0065159 A1 | | 3/2011 | Raines et al. |
| 2013/0034891 A1 | | 2/2013 | Fanselow et al. |
| 2014/0107355 A1 | | 4/2014 | Dumesic et al. |
| 2014/0349351 A1 | | 11/2014 | Jensen et al. |
| 2015/0274685 A1 | | 10/2015 | Dumesic et al. |

FOREIGN PATENT DOCUMENTS

WO    WO 2016/106094    6/2016

OTHER PUBLICATIONS

Qi et al., "Efficient process for conversion of fructose to 5-hydroxymethylfurfural with ionic liquids", Green Chem., 2009, vol. 11, pp. 1327-1331. DOI: 10.1039/b905975j.*
Liu et al., "A novel route towards high yield 5-hydroxymethylfurfural from fructose catalyzed by a mixture of Lewis and Bronsted acids", RSC Adv., 2014, vol. 4, pp. 42035-42038. DOI: 10.1039/c4ra04906c.*
Huang et al., "Integrating enzymatic and acid catalysis to convert glucose into 5-hydroxymethylfurfural", Chem. Commun., 2010, vol. 46, pp. 1115-1117. DOI: 10.1039/b921306f.*
Moreau et al., "Dehydration of fructose and sucrose into 5-hydroxymethylfurfural in the presence of 1-H-3-methyl imidazolium chloride acting both as solvent and catalyst", Journal of Molecular Catalysis A: Chemical 253 (2006) 165-169. doi:10.1016/j.molcata.2006.03.046.*
Xiao et al., "Efficient catalytic conversion of the fructose into 5-hydroxymethylfurfural by heteropolyacids in the ionic liquid of 1-butyl-3-methyl imidazolium chloride", Applied Catalysis A: General 484 (Jul. 2014) 74-78.*
Qu et al., "Efficient dehydration of fructose to 5-hydroxymethylfurfural catalyzed by a recyclable sulfonated organic heteropolyacid salt", Bioresource Technology 106 (2012) 170-172.*
Binder et al., "Fermentable sugars by chemical hydrolysis of biomass", PNAS, 2010, 107(10):4516-4521.*
Bao, et al., "Preparation of 5-hydroymethylfurfural by dehydration of fructose in the presence of acidic ionic liquid," Catalysis Communications 9, (Jan. 25, 2008), 6 pages.
Binder, et al., "Simple Chemical Transformation of Lignocellulosic Biomass into Furans for Fuels and Chemicals," J. Am. Chem. Soc. 2009, (Oct. 30, 2008), 7 pages.
Caes, "Catalytic Systems for Carbohydrate Conversions," Dissertation from University of Wisconsin—Madison, (Jul. 27, 2012), 196 pages.
Eminov, et al., "Highly selective and near-quantitative conversion of fructose to 5-hydroxymethylfurfural using mildly acidic ionic liquids," ACS Sustainable Chem. Eng., (Feb. 13, 2014), 18 pages.
Huang, et al., "Tandem Catalytic Conversion of Glucose to 5-Hydroxymethylfurfural with an Immobilized Enzyme and a Solid Acid," ACS Catalysis, (Jun. 3, 2014), 4 pages.

(Continued)

*Primary Examiner* — Suzanne M Noakes
(74) *Attorney, Agent, or Firm* — Weaver Austin Villeneuve & Sampson LLP (57) ABSTRACT

Methods of converting lignocellulosic derivatives form 5-hydroxymethyl furfural (HMF) in ionic liquids are provided herein. Glucose is enzymatically converted to fructose by isomerization with glucose isomerase and a borate salt. Conversion of fructose to HMF includes dehydration of fructose using ionic liquids or ionic liquids with an acid catalyst to achieve high yield of HMF.

8 Claims, 6 Drawing Sheets

(56) References Cited

OTHER PUBLICATIONS

Karinen, et al., "Biorefining: Heterogeneously Catalyzed Reactions of Carbohydrates for the Production of Furfural and Hydroxymethylfurfural," ChemSusChem, (2011), 15 pages.
Lewkowski, "Synthesis, chemistry and applications of 5-hydroxymethylfurfural and its derivatives," ARKIVOC, (Aug. 8, 2001), 38 pages.
Li, et al., "Efficient Acid-Catalyzed Hydrolysis of Cellulose in Ionic Liquid," Adv. Synth. Catal., (May 24, 2007), 11 pages.
Li, et al., "The dehydration of fructose to 5-hydroxymethylfurfural efficiently catalyzed by acidic ion-exchange resin in ionic liquid," Bioresource Technology 133, (Jan. 22, 2013), 7 pages.
Matsagar, et al., "Conversion of concentrated sugar solutions in to 5-hydroxymethyl furfural and furfural using Brönsted acidic ionic liquids," Catalysis Science & Technology, (2013), 5 pages.
Rendleman, et al., "Complexes of Carbohydrates With Aluminate Ion. Aldoseketose Interconversion on Anion-Exchange Resin (Aluminate and Hydroxide Forms)," Carbohydrate Research, (Oct. 20, 1978), 17 pages.
van Putten, et al., "Hydroxymethylfurfural, A Versatile Platform Chemical Made from Renewable Resources," Chemical Reviews, (2013), 99 pages.
Zhang, et al., "Highly efficient conversion of microcrystalline cellulose to 5-hydroxymethyl furfural in a homogeneous reaction system," RSC Advances, (Feb. 16, 2016), 5 pages.
PCT International Search Report and Written Opinion, dated Aug. 24, 2016, issued in PCT/US2015/066474.
PCT International Preliminary Report on Patentability and Written Opinion, dated Jun. 27, 2017, issued in PCT/US2015/066474.
Chen, et al. "Conversion of fructose into 5-hydroxymethylfurfural catalyzed by recyclable sulfonic acid-functionalized metal-organic frameworks," Green Chem., 2014, 16, 2490-2499, Jan. 8, 2014, 10 pages.
Guo, et al. "Conversion of fructose and glucose into 5-hydroxymethylfurfural with lignin-derived carbonaceous catalyst under microwave irradiation in dimethyl sulfoxide-ionic liquid mixtures," Bioresource Technology 112 (2012) 313-318, Feb. 23, 2012, 6 pages.
Zhao, et al. "Metal Chlorides in Ionic Liquid Solvents Convert Sugars to 5-Hydroxymethylfurfural," Science Mag, vol. 316, Jun. 15, 2007, 4 pages.
Zi, et al. "Catalytic hydrothermal conversion of carboxymethyl cellulose to value-added chemicals over metal-organic framework MIL-53(A1)," Carbohydrate Polymers 115 (2015) 146-151, Aug. 13, 2014, 6 pages.
U.S. Appl. No. 15/539,122, filed Jun. 22, 2017, Sathitsuksanoh, et al.

* cited by examiner

HMF PRODUCTION FROM GLUCOSE IN IONIC LIQUID MEDIA

CROSS-REFERENCE TO RELATED APPLICATION

This application claims benefit of U.S. Provisional Patent Application No. 62/096,458, filed Dec. 23, 2014, and titled "HMF PRODUCTION FROM FRUCTOSE IN IONIC LIQUID MEDIA," which is incorporated by reference herein in its entirety and for all purposes.

STATEMENT OF GOVERNMENTAL SUPPORT

This invention was made with government support under Contract No. DE-AC02-05CH11231 awarded by the U.S. Department of Energy. The government has certain rights in the invention.

BACKGROUND

Biomass resources are used in various industrial applications to provide renewable energy sources. Cellulose from lignocellulose is the most abundant bioresource on the planet. Cellulose includes glucose building blocks, which may be converted to other derivatives for use as a biofuel and chemicals in various industries.

SUMMARY

Provided herein are methods of processing lignocellulosic derivatives. One aspect involves a method of processing a lignocellulosic derivative by converting fructose to 5-hydroxymethyl furfural by introducing an ionic liquid to fructose.

The method may further include, prior to converting the fructose to 5 hydroxymethyl furfural, enzymatically converting glucose to the fructose. Enzymatically converting glucose to fructose may further include introducing glucose isomerase and a borate salt to glucose.

The method may further include introducing an acid catalyst. The acid catalyst may include aluminum chloride.

In some embodiments, the ionic liquid includes C2mim. In some embodiments, the percent yield of 5-hydroxymethyl furfural is at least about 50% in weight. In some embodiments, the selectivity of 5-hydroxymethyl furfural is at least about 60% in weight.

These and other aspects are described further below with reference to the drawings.

DETAILED DESCRIPTION

In the following description, numerous specific details are set forth to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

The production of biofuels and chemicals provides resources to various industries. Biofuels may be formed by biomass conversion, or in particular, lignocellulosic biomass conversion. Example types of lignocellulosic biomass include aromatic polymers, such as lignin, and carbohydrate polymers, such as cellulose and hemicellulose.

Cellulose from lignocellulose is the most abundant bioresource on the planet and processes to convert cellulose into compounds may be suitable for use in many industries. In particular, cellulose may be used as a feedstock to form other compounds. Cellulose consists mainly of glucose building blocks. Various industries use conversion of glucose to other compounds as a precursor to producing chemicals and materials in industrial processes.

The production of fuels and chemicals from lignocellulose-derived 5-hydroxymethyl furfural (HMF) is of particular interest, since HMF can be further converted to $C_9$-$C_{15}$ alkanes, 2,5-dimethylfuran, ethyl levulinate, 5-(alkoxymethyl)furfurals, and 2,5-bis(alkoxymethyl)furans. Conversion of glucose to HMF may occur via a dehydration reaction, or via formation of an intermediate such as fructose.

Figure 1:
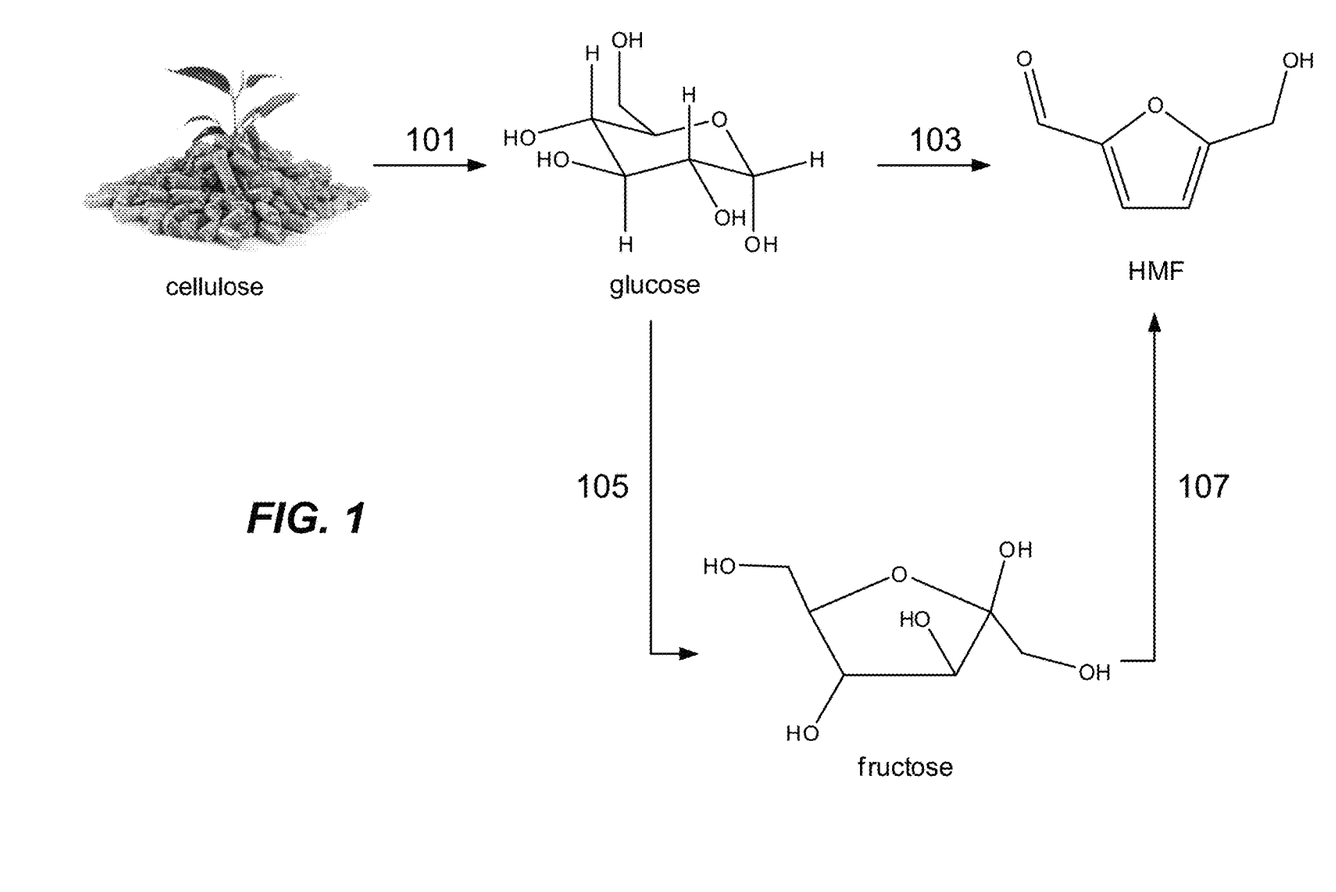
FIG. 1 depicts reaction pathways for forming 5-hydroxymethyl furfural from cellulose.

FIG. 1 depicts example pathways for forming HMF. As shown, cellulose may break down into glucose via reaction 101, a hydrolysis reaction. After glucose is formed, glucose may undergo reaction 103 to directly form HMF—this reaction includes a dehydration mechanism. Alternatively, glucose may undergo reaction 105 to form fructose as an intermediate. This may be performed by isomerization of glucose. Subsequently, fructose may undergo reaction 107 to form HMF, the reaction of which may include dehydration. In various processes, the conversion from glucose to HMF via reactions 105 and 107 may occur quickly such that fructose may go undetected.

In some processes, humin by-products may be formed. Humins may be heterogeneous undesired waste. For example, humins may be formed in the conversion from cellulose to glucose, or glucose to fructose, or glucose to HMF, or fructose to HMF. The amount of material A that is converted in a reaction may have reacted to form waste by-products or other compounds in addition to a desired product. As used herein, a percent conversion or percent converted of a material A is defined as the amount of A that reacted or converted divided by initial amount of A used in the reaction. Thus, the percent conversion includes production of desired products as well as production of humins.

In processes described herein, the selectivity for a reaction mechanism to form a specific product may be determined. In a reaction where A is reacted to form B, and B is the specific, desired product, the reaction may also form some other by-products C. In some reactions, some of A may be unreacted, such that a post-reaction mixture includes B, C, and some A. The selectivity of a chemical or reaction mechanism is defined as the amount of B, a specific product, divided by the amount of A reacted to form a new product, desired or otherwise; referred to above as converted. That is, selectivity of a specific product may be defined as how much specific product is formed from the total amount of the initial reactant that converted. A higher selectivity indicates that there is less undesirable product formation.

As an example, a reaction may include converting A to B using a catalyst, with some excess by-product C:

In such an example, 10 moles of A may be mixed with a catalyst to form 4 moles of B and 1 mole of C. If the resulting mixture of A, B, and C includes 2 moles of A, then only 8 moles of A was converted or reacted in the reaction. Thus, the percent conversion of A is:

$$\text{Percent Conversion of } A = \frac{8 \text{ moles converted}}{10 \text{ moles initial}} \times 100\% = 80\%$$

If the resulting mixture of A, B, and C includes 4 moles of B after having converted 8 moles of A, then the selectivity of B is:

$$\text{Selectivity of } B = \frac{4 \text{ moles of } B \text{ product}}{8 \text{ moles of } A \text{ converted}} \times 100\% = 50\%$$

Note that as a result, processes described herein may focus on maximizing selectivity rather than maximizing percent conversion because even if percent conversion of A is high, if selectivity to form B is low, then the process efficiency for obtaining B is low, as a substantial amount of A may be converted to a waste by-product C (e.g., a humin) from which it is not possible to generate the desired product B further. If percent conversion of A is low, but selectivity to form B is high, then the process efficiency for obtaining B is high, since the amount of A that is not converted may be recycled and used in the process again to form B. A higher selectivity of B suggests less by-products C are formed, so high selectivity is useful in achieving a more efficient and economical process.

Provided herein are methods of processing lignocellulosic derivatives using ionic liquids to achieve high selectivity for the formation of HMF. Ionic liquids may be used as a catalyst or as a solvent with an acid catalyst. Methods may yield HMF selectivity greater than about 80 mol %, for example, greater than about 85 mol %, or greater than about 86 mol %, with percent conversion near 100%.

Figure 2:
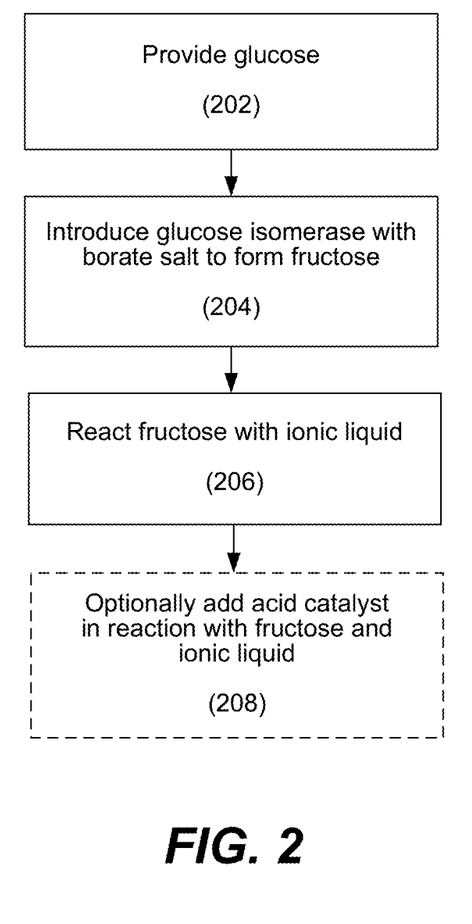
FIG. 2 is a process flow diagram depicting operations for performing a method in accordance with disclosed embodiments.

FIG. 2 is a process flow diagram depicting operations for a method in accordance with disclosed embodiments. In operation 202, a lignocellulosic derivative is provided, for example, to a stirred tank reactor. The lignocellulosic derivative may be formed by converting cellulose via an acidolysis or acid hydrolysis mechanism. For example, cellulose may be pretreated with a solvent and reacted with an acid such as HCl over time (such as about 1 hour) to slowly convert cellulose to glucose without polymerizing the lignocellulosic derivative. In one example, about 15 grams of feedstock is pretreated in a solvent of 1-n-butyl-3-methylimidazolium chloride ([C$_4$mim]Cl) at 140° C. for an hour, and the cellulose undergoes acid hydrolysis in 85 g of [C$_4$mim]Cl slowly over 1 hour while maintaining a low pH of about 1. The lignocellulosic derivative may be a monosaccharide, or in some embodiments, an oligosaccharide or polysaccharide. In various embodiments, the lignocellulosic derivative is glucose. In some embodiments, conversion of cellulose to glucose may achieve a glucose yield between about 93 wt % and 96 wt %. In various embodiments, the solvent used to break down biomass to a lignocellulosic derivative completely dissolves the biomass. In some examples, the solvent is [C$_4$mim]Cl.

In operation 204, glucose is catalyzed by glucose isomerase and a borate salt to form fructose via an enzymatic pathway. Note that although the example provided in FIG. 2 converts glucose into fructose, an alternative lignocellulosic derivative may be formed using a different reactant and/or catalyst. Here, fructose may be formed by converting glucose using an enzymatic pathway.

Figure 3:
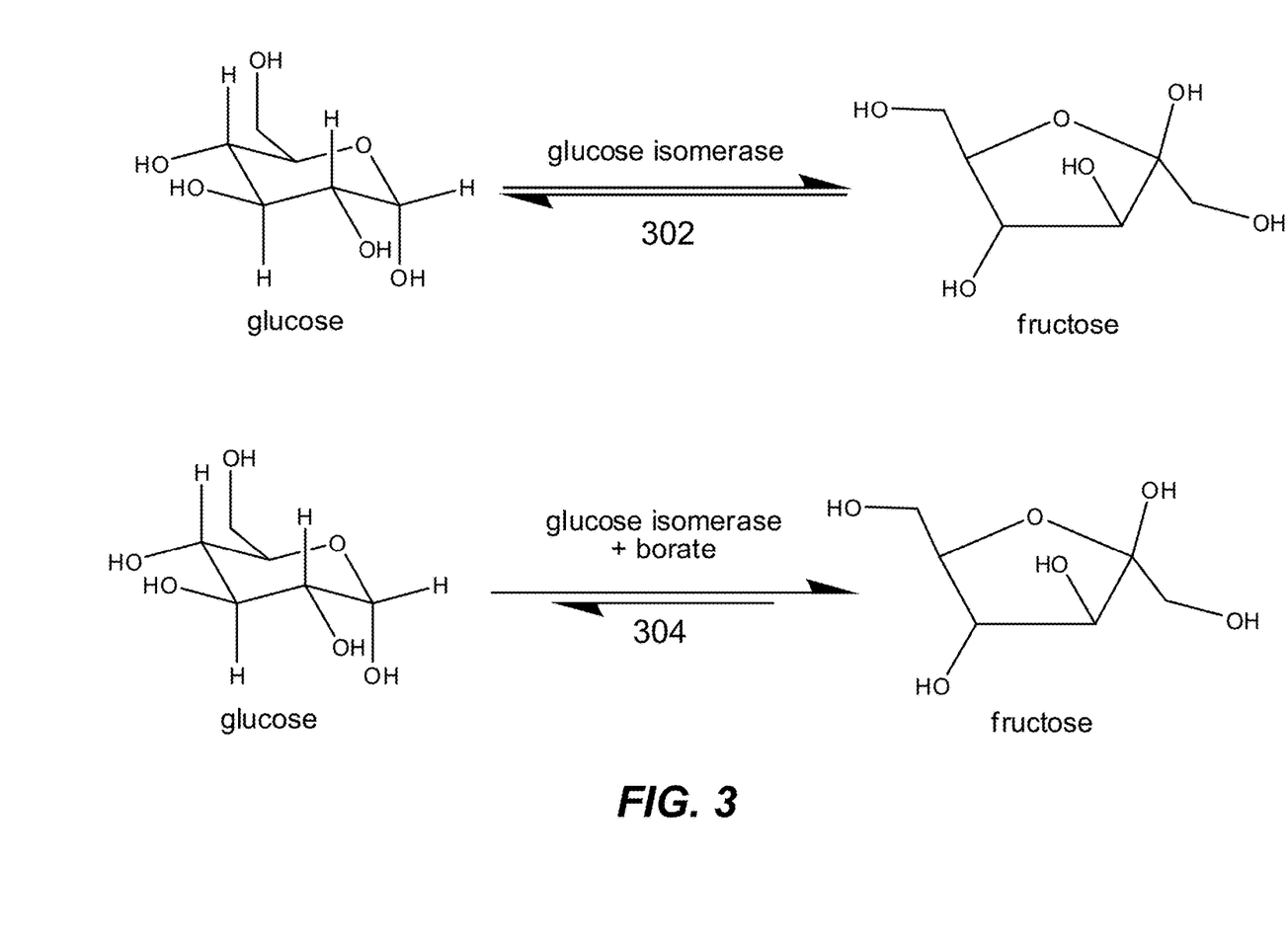
FIG. 3 depicts reactions for conversions between glucose and fructose.

FIG. 3 shows a reaction 302 whereby glucose isomerase catalyzes conversions between glucose and fructose. Since the reaction involving glucose isomerase is a reversible reaction and glucose and fructose are isomers of each other, equal amounts of glucose and fructose are present at equilibrium. That is, a reaction mixture that starts with glucose and catalyzed by glucose isomerase may form a mixture with 50% glucose and 50% fructose. In some embodiments, reaction 304 may be used instead of reaction 302 to yield more fructose. That is, a borate salt such as boric acid (H$_3$BO$_3$) or sodium borate (Na$_2$B$_4$O$_7$.10H$_2$O) may be added to the reaction mixture. Without being bound by a particular theory, borate salts may form a complex with fructose, thereby hampering glucose isomerase's function to isomerize fructose back to glucose. In some embodiments, adding sodium borate may form about 70% fructose and about 30% glucose.

Figure 4:
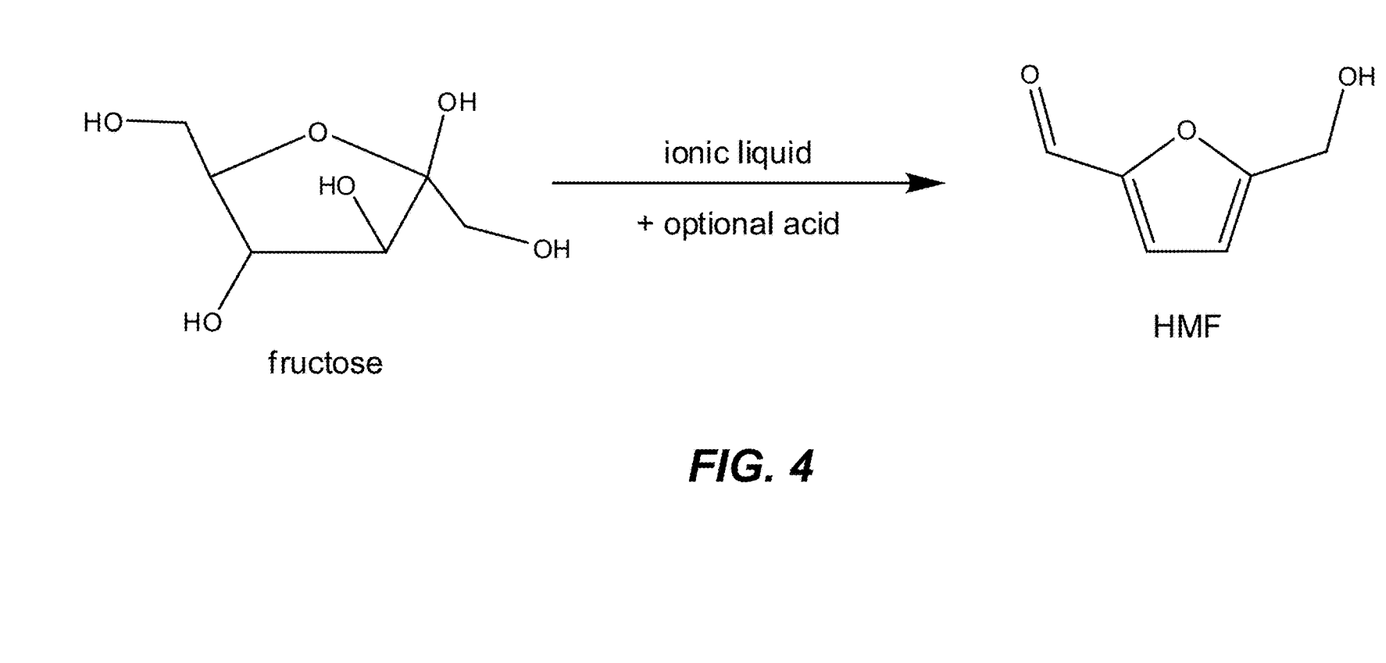
FIG. 4 depicts a reaction for forming 5-hydroxymethyl furfural in accordance with disclosed embodiments.
Figure 5:
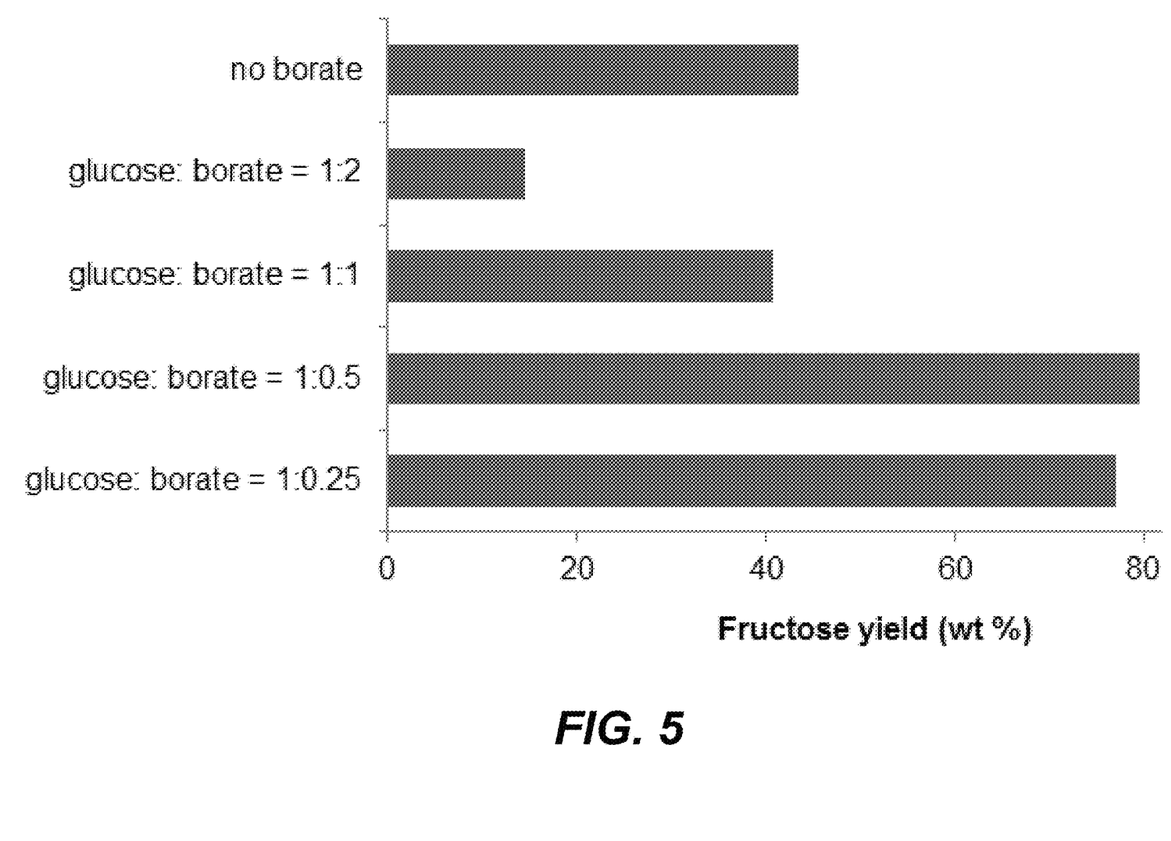
FIGS. 5 and 6 are graphs of experimental results from performing methods in accordance with disclosed embodiments.

Returning to FIG. 2, in operation 206, fructose is mixed with an ionic liquid. The reaction may be as shown in FIG. 4. In various embodiments, the ionic liquid is an acidic ionic liquid. Ionic liquids may include 1-ethyl-3-methylimidazolium chloride (C$_2$mim), 1-propyl-3-methylimidazolium chloride (C$_3$mim), and 1-butyl-3-methylimidazolium chloride (C$_4$mim), and other acidic ionic liquids.

Other suitable IL that can be used in the disclosed embodiments include any IL that converts fructose to HMF. In some embodiments, the IL is also suitable for pretreatment of biomass and for the hydrolysis of cellulose by thermostable cellulase. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, where an "alkyl" is an alkyl group including from 1 to 10 carbon atoms, and an "alkanate" is an alkanate including from 1 to 10 carbon atoms. In some embodiments, the "alkyl" is an alkyl group including from 1 to 4 carbon atoms. In some embodiments, the "alkyl" is a methyl group, ethyl group or butyl group. In some embodiments, the "alkanate" is an alkanate including from 1 to 4 carbon atoms. In some embodiments, the "alkanate" is an acetate. In some embodiments, the halide is chloride.

Additional suitable IL include, but are limited to, 1-ethyl-3-methylimidazolium acetate (EMIM Acetate), 1-ethyl-3-methylimidazolium chloride (EMIM Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and the like. The ionic liquid can include one or a mixture of the compounds. Further ILs are described in U.S. Pat. No. 6,177,575 (which is herein incorporated by reference), which describes ILs having the following structure:

whereby R$^1$, R$^2$ and R$^3$ are each independently hydrogen, hydrocarbyl or substituted hydrocarbyl; and R$^4$ is hydrogen, alkyl, or substituted alkyl.

In various embodiments, the ionic liquid acts as a catalyst to convert fructose to HMF. For example, in operation 206, fructose may be mixed with C$_2$mim, whereby C$_2$mim acts as a catalyst to convert fructose to HMF. In some embodiments, at least about 90% of fructose may be converted to HMF using an ionic liquid as a catalyst. In some embodiments, HMF yield may be at least about 50 wt %. In some embodiments, operation 206 may be performed at a temperature between about 60° C. and about 120° C.

In various embodiments, the ionic liquid is a solvent and an acid catalyst is optionally added in operation 208 to convert fructose to HMF. The acid catalyst may be a Lewis or Brønsted acid, a polyacid, or a solid acid catalyst. Example Lewis and Brønsted acid, polyacid, and solid acid catalysts include AlCl$_3$ 6H$_2$O, CrCl$_3$ 6H$_2$O, SnCl$_4$ 2H$_2$O, 12-MPA, 12-TPA, and dilute H$_3$PO$_4$, such as 30% H$_3$PO$_4$. Acid catalyzed conversion of fructose to HMF may be performed at a temperature of about 100° C. for a duration of at least about 20 minutes. In some embodiments, operation 206 may be performed for a time between about 15 minutes and about 120 minutes. The HMF yield may be at least about 50 weight percent, and at least about 90% of fructose may be converted. For example, about 98% of fructose may be converted in operation 208.

In some embodiments, some unreacted fructose may remain after reacting with the ionic liquid or acid catalyst. HMF and any undesired humin by-products may be extracted from the mixture, and unreacted fructose may be further catalyzed by an ionic liquid or acid catalyst to drive further formation of HMF. Selectivity may be at least about 60 wt % or at least about 80 mol %, such as about 86 mol %. For example, 100% fructose converted from recycling unreacted fructose may yield about 60 g of HMF per 100 g of fructose.

The HMF yield in weight percent for converting fructose using an ionic liquid without an acid catalyst for about 20 minutes may be at least about 40 wt %. For a reaction over 30 minutes, the HMF yield may be at least about 50 wt %. For a duration of about 90 minutes, HMF yield in weight percent for converting fructose using an ionic liquid without an acid catalyst may be at least about 50%, such as about 58%.

The HMF yield in weight percent for converting fructose using an ionic liquid with an acid catalyst for about 20 minutes may be at least about 20% or at least about 40%, or at least about 50%, such as about 49%. For a duration of about 90 minutes, HMF yield in weight percent for conversion using an ionic liquid with an acid catalyst may be at least about 40%, or at least about 55%, such as about 56%.

EXPERIMENTAL

Experiment 1

Glucose Isomerization

An experiment was conducted to evaluate the effect of using a borate salt in a conversion reaction between glucose and fructose. Five trials were conducted, each having varying amounts of sodium borate. In each trial, 600 mg of glucose was mixed with 18 mg of Sweetzyme®, a ready-immobilized glucose isomerase available from Novozymes of Denmark and 10 mg of magnesium sulfate (MgSO$_4$) in 5 mL of water H$_2$O at a temperature of 70° C. in a 500 mL stirred tank reactor such as 500 mL HP/HT reactors from the 4570 Series, available from Parr Instrument Company of Moline, Ill. The first trial did not use sodium borate, and the subsequent trials used borate such that the glucose to borate ratios by molar ratio were 1:2, 1:1, 1:0.5, and 1:0.25. The results are summarized in Table 1 below.

TABLE 1

Effect of borate on glucose isomerization

| Glucose to Borate Ratio | | | Time (hr) | | | | | | |
|---|---|---|---|---|---|---|---|---|---|
| | | | 2 | 4 | 6 | 8 | 10 | 24 | 52 |
| 1:2 | Conv. | (%) | 1.42 | 7.86 | 17.85 | 17.53 | 16.57 | 38.54 | 60.62 |
| | Fructose | (%) | 6.58 | 9.69 | 11.25 | 13.08 | 14.5 | 14.39 | 11.06 |
| | Selectivity | (%) | 463.0 | 123.4 | 63.1 | 74.6 | 87.5 | 37.3 | 18.3 |
| 1:1 | Conv. | (%) | 22.88 | 23.18 | 31.39 | 39.89 | 41.85 | 66.69 | 71.00 |
| | Fructose | (%) | 13.71 | 25.19 | 33.08 | 37.36 | 42.71 | 40.81 | 27.89 |
| | Selectivity | (%) | 59.9 | 108.7 | 105.4 | 93.7 | 102.1 | 61.2 | 39.3 |
| 1:0.5 | Conv. | (%) | 27.34 | 48.28 | 62.25 | 69.49 | 75.41 | 79.59 | 88.47 |
| | Fructose | (%) | 26.48 | 45.26 | 57.34 | 65.29 | 70.66 | 79.59 | 61.76 |
| | Selectivity | (%) | 96.9 | 93.7 | 92.1 | 94.0 | 93.7 | 100.0 | 69.8 |

TABLE 1-continued

Effect of borate on glucose isomerization

| Glucose to Borate Ratio | | | 2 | 4 | Time (hr) 6 | 8 | 10 | 24 | 52 |
|---|---|---|---|---|---|---|---|---|---|
| 1:0.25 | Conv. | (%) | 39.32 | 63.64 | 74.37 | 78.23 | 78.3 | 77.11 | 81.39 |
| | Fructose | (%) | 33.84 | 52.32 | 60.00 | 63.05 | 70.47 | 77.11 | 64.03 |
| | Selectivity | (%) | 86.1 | 82.2 | 80.7 | 80.6 | 90.0 | 100.0 | 78.7 |
| no borate | Conv. | (%) | 37.32 | 44.97 | 50.54 | 47.26 | 47.11 | 43.34 | 51.67 |
| | Fructose | (%) | 30.82 | 39.24 | 37.47 | 40.29 | 40.53 | 43.34 | 37.2 |
| | Selectivity | (%) | 82.6 | 87.2 | 74.1 | 85.2 | 86.0 | 100.0 | 72.0 |

Table 1 shows the percent conversion of glucose to fructose, fructose yield, and selectivity for fructose in each trial. FIG. 4 shows a bar graph depicting fructose yield for each trial. As shown, using a glucose to borate ratio of 1:0.5 and 1:0.25 yielded the most amount of fructose—that is, the reaction mixture had more fructose than glucose, suggesting the borate salt may have interacted with the mixture such that glucose isomerase is hindered from converting fructose back to glucose. Selectivity for fructose was also particularly high at these ratios (over 80%).

The effect of pH on glucose isomerization with a glucose to borate ratio of 1:0.5 was evaluated for pH at 4, 5, 6, 7, and 8. The results are summarized in Tables 2A, 2B, and 2C below. In this experiment, pH from 4-8 had little to no effect on glucose conversion and fructose selectivity.

TABLE 2A

Glucose Isomerization at pH = 4, 5

| | pH 4 | | | pH 5 | | |
|---|---|---|---|---|---|---|
| Time (hr) | Conv. (%) | Yield (%) | Sel. (%) | Conv. (%) | Yield (%) | Sel. (%) |
| 2 | 31.3 | 28.1 | 89.7 | 28.6 | 30.2 | 105.4 |
| 4 | 50.2 | 49.2 | 98.1 | 51.9 | 48.1 | 92.7 |
| 6 | 66.1 | 59.1 | 89.5 | 66.5 | 59.7 | 89.7 |
| 8 | 73.4 | 66.2 | 90.2 | 72.9 | 69.4 | 95.3 |
| 10 | 78.5 | 70.8 | 90.2 | 78.5 | 73.4 | 93.6 |
| 24 | 80.3 | 80.3 | 100.0 | 80.7 | 80.7 | 100.0 |
| 52 | 88.5 | 57.3 | 64.8 | 88.1 | 61.1 | 69.4 |

TABLE 2B

Glucose Isomerization at pH = 6, 7

| | pH 6 | | | pH 7 | | |
|---|---|---|---|---|---|---|
| Time (hr) | Conv. (%) | Yield (%) | Sel. (%) | Conv. (%) | Yield (%) | Sel. (%) |
| 2 | 26.6 | 31.8 | 119.3 | 25.0 | 33.8 | 135.1 |
| 4 | 48.2 | 55.4 | 114.9 | 53.2 | 52.3 | 98.3 |
| 6 | 65.5 | 66.3 | 101.3 | 67.5 | 65.1 | 96.4 |
| 8 | 73.0 | 74.0 | 101.4 | 75.3 | 69.6 | 92.4 |
| 10 | 80.1 | 72.6 | 90.6 | 80.5 | 72.2 | 89.8 |
| 24 | 81.5 | 81.5 | 100.0 | 81.3 | 81.3 | 100.0 |
| 52 | 88.3 | 62.0 | 70.2 | 88.8 | 56.9 | 64.0 |

TABLE 2C

Glucose Isomerization at pH = 8

| | pH 8 | | |
|---|---|---|---|
| Time (hr) | Conv. (%) | Yield (%) | Sel. (%) |
| 2 | 25.9 | 29.3 | 113.0 |
| 4 | 49.8 | 52.3 | 105.2 |
| 6 | 67.1 | 62.5 | 93.0 |
| 8 | 73.4 | 73.3 | 99.9 |
| 10 | 79.9 | 74.3 | 93.0 |
| 24 | 82.0 | 82.0 | 100.0 |
| 52 | 88.3 | 63.4 | 71.8 |

In Tables 1, 2A, 2B, and 2C, the glucose to fructose percent conversion is evaluated by:

$$\text{Percent Conversion of Glucose} = \frac{\text{Amount of glucose reacted}}{\text{Amount of initial glucose}} \times 100\%$$

Fructose yield is calculated by:

$$\text{Fructose Yield} = \frac{\text{Amount of fructose produced}}{\text{Amount of initial glucose}} \times 100\%$$

The selectivity for fructose is calculated by:

$$\text{Selectivity of Fructose} = \frac{\text{Amount of fructose produced}}{\text{Amount of glucose reacted}} \times 100\%$$

Experiment 2

Fructose Conversion to HMF Using Ionic Liquid as a Catalyst

An experiment was conducted to evaluate the effect of using an ionic liquid as a catalyst to convert fructose to HMF. Three trials were performed, using 1-ethyl-3-methylimidazolium chloride ([$C_2$mim]Cl), 1-propyl-3-methylimidazolium chloride ([$C_3$mim]Cl), and 1-butyl-3-methylimidazolium chloride ([$C_4$mim]Cl). Fructose percent conversion and HMF yield were calculated for each trial. In each trial, 1 mmol of fructose was mixed with 10 mol % of the ionic liquid catalyst at a temperature of 100° C. for various durations over 90 minutes. The results are summarized in Table 3 below.

TABLE 3

Reaction Time for Ionic Liquid Catalyzed Conversion of Fructose to HMF

| | [C₂mim]Cl | | [C₃mim]Cl | | [C₄mim]Cl | |
|---|---|---|---|---|---|---|
| Time (min) | Conv (%) | HMF yield (wt. %) | Conv (%) | HMF yield (wt. %) | Conv (%) | HMF yield (wt. %) |
| 10 | 67.39 | 26.95 | 12.50 | 1.72 | 8.37 | 0.20 |
| 20 | 85.06 | 47.82 | 28.98 | 5.86 | 14.79 | 1.52 |
| 30 | 94.23 | 56.74 | 39.85 | 11.56 | 21.34 | 3.86 |
| 45 | 96.12 | 52.39 | 63.06 | 29.35 | 30.06 | 9.68 |
| 60 | 99.31 | 59.53 | 65.60 | 33.49 | 41.58 | 14.20 |
| 90 | 99.29 | 58.60 | 91.00 | 52.95 | 54.84 | 21.28 |

As shown in Table 3, [C₂mim]Cl and [C₃mim]Cl showed surprisingly high HMF yields and percent conversions without using an acid catalyst. These results also suggest [C₄mim]Cl may be largely unreactive alone in converting fructose to HMF, yielding only 21.28 wt % after 90 minutes into the reaction.

Experiment 3

Fructose Conversion to HMF Using Acid Catalyst and Ionic Liquid

An experiment was conducted to evaluate the effect of using various acid catalysts to convert fructose to HMF. Seven trials were performed, including one control trial. The following acid catalysts were tested: AlCl₃ 6H₂O, CrCl₃ 6H₂O, SnCl₄ 2H₂O, 12-MPA, 12-TPA (12-O-tetradecanoyl-phorbol-13-acetate), and 30% H₃PO₄. CrCl₃, SnCl₄, and AlCl₃ were loaded at the loading of 10 mol % catalyst and 12-MPA, 12-TPA, and 30% H₃PO₄ were loaded at 1 mol % catalyst. Fructose percent conversion, HMF yield, and HMF selectivity were calculated for each trial. In each trial, 1 mmol of fructose was mixed with 10 mol % of the catalyst in 15 mmol of [C₄mim]Cl solvent at a temperature of 100° C. for 20 minutes. The results are summarized in Table 4 below.

TABLE 4

Fructose Conversion using Acid Catalyst

| Catalyst | Feed | Solvent | Fructose conversion (%) | HMF yield (wt. %) | HMF selectivity (mol %) |
|---|---|---|---|---|---|
| CrCl₃ 6H₂O | Fructose | [C₄mim]Cl | 90.20 | 37.87 | 60.04 |
| SnCl₄ 2H₂O | Fructose | [C₄mim]Cl | 58.88 | 14.45 | 35.09 |
| AlCl₃ 6H₂O | Fructose | [C₄mim]Cl | 97.66 | 56.12 | 82.17 |
| 12-TPA | Fructose | [C₄mim]Cl | 53.82 | 27.86 | 74.02 |
| 12-MPA | Fructose | [C₄mim]Cl | 97.55 | 43.35 | 63.55 |
| 30% H₃PO₄ | Fructose | [C₄mim]Cl | 9.64 | 1.19 | 17.65 |
| no cat | Fructose | [C₄mim]Cl | 6.48 | 0.29 | 6.40 |

The fructose to HMF percent conversion is evaluated by:

$$\text{Percent Conversion of Fructose} = \frac{\text{Amount of fructose reacted}}{\text{Amount of initial fructose}} \times 100\%$$

HMF yield is calculated by:

$$\text{HMF Yield} = \frac{\text{Amount of HMF produced}}{\text{Amount of initial fructose}} \times 100\%$$

Figure 6:
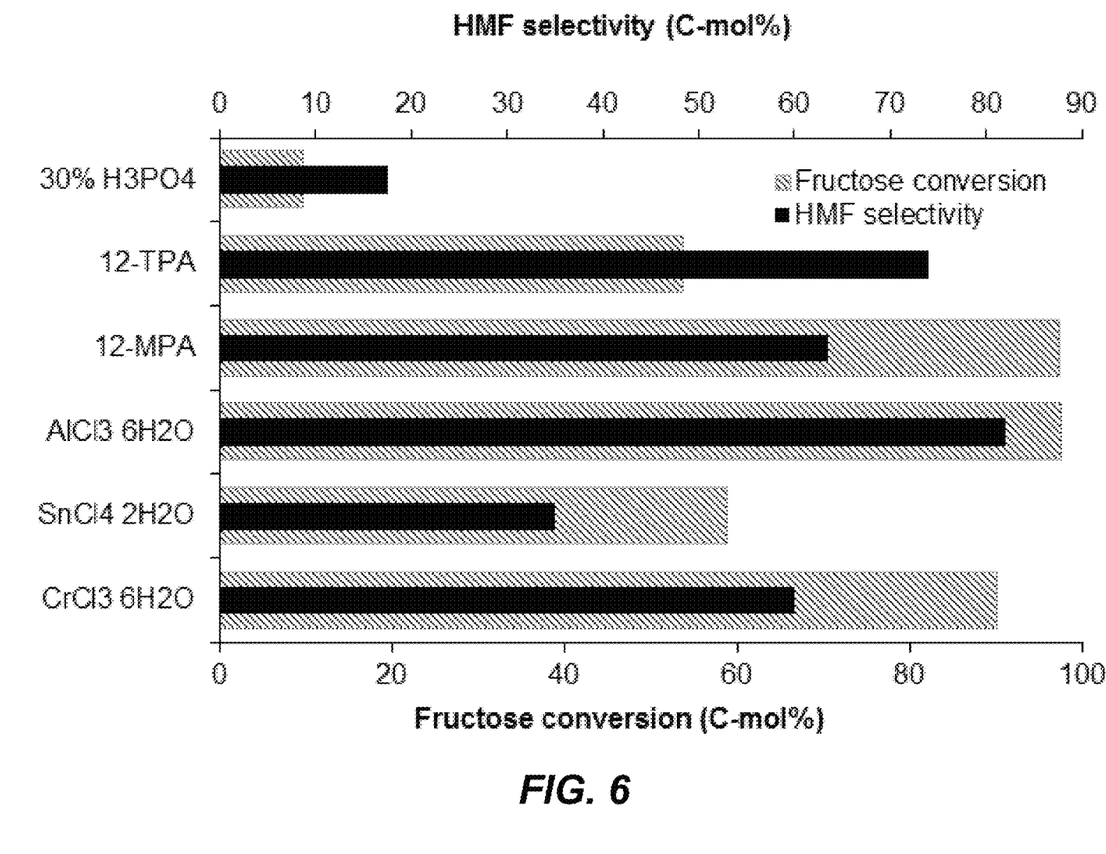

FIG. 6 is a bar graph depicting HMF selectivity in mol % and fructose conversion in mol % for each tested trial. As shown, AlCl₃ 6H₂O showed high promise for high HMF selectivity and high fructose conversion, suggesting that fewer cycles would be needed to fully convert fructose to HMF. Another possibly suitable option was 12-TPA, which had high HMF selectivity. Although fructose conversion was about 50%, unconverted fructose may be recycled and reacted with 12-TPA again in subsequent cycles to fully convert fructose to HMF.

Conversion and yield were also calculated for various durations, such as at 10 minutes, 30 minutes, 45 minutes, 60 minutes, and 90 minutes for 12-MPA, 12-TPA, and AlCl₃ 6H₂O trials. For Table 5, 1 mol % of 12-MPA and 1 mol % of 12-TPA were used, while 2.5 mol % of AlCl₃ 6H₂O was used to convert fructose into HMF. The conversion and yield values are summarized in Table 5 below.

TABLE 5

Reaction Time for Acid Catalyzed Conversion of Fructose to HMF

| | 12-MPA | | 12-TPA | | AlCl₃ 6H₂O | |
|---|---|---|---|---|---|---|
| Time (min) | Conv (%) | HMF yield (wt. %) | Conv (%) | HMF yield (wt. %) | Conv (%) | HMF yield (wt. %) |
| 10 | 27.67 | 6.70 | 21.76 | 6.52 | 42.58 | 20.90 |
| 20 | 30.26 | 8.17 | 53.82 | 27.86 | 87.32 | 49.50 |
| 30 | 91.80 | 41.18 | 71.05 | 38.96 | 94.93 | 53.59 |
| 45 | 82.74 | 42.26 | 79.82 | 47.15 | 99.35 | 55.67 |
| 60 | 93.48 | 48.29 | 92.09 | 48.86 | 99.39 | 55.81 |
| 90 | 95.97 | 49.73 | 96.95 | 53.81 | 99.45 | 56.03 |

As shown, after about 30 minutes or 45 minutes, AlCl₃ 6H₂O approaches about 100% conversion, and 12-MPA and 12-TPA show similar trends at about 60 minutes or 90 minutes. AlCl₃ 6H₂O has the highest HMF yield of the three acid catalysts but all include yields at least about 40% after about 45 minutes.

Experiment 4

Example Pathway from Cellulose to HMF

Experiments were conducted to measure HMF production using methods described in accordance with disclosed embodiments. 15 g of cellulose was pretreated with 85 g of [C₄mim]Cl at 140° C. for 1 hour with 15 wt % solid loading, followed by acid hydrolysis using HCl to convert cellulose to glucose. From 100 g of cellulose, 96.2 g of glucose and 10.2 g of HMF were formed. The glucose produced in the acidolysis reaction was then reacted with glucose isomerase and sodium borate with a mole ratio of glucose to borate of 1:0.5 at 70° C. for 10 hours. This isomerization yielded 76.6 g of fructose and 19.6 g of glucose. Trials were performed to convert fructose to HMF. Each reaction was performed without recycling any unreacted fructose. In the first trial, 180 mg fructose that was converted from the prior isomerization was reacted with 2 g of [C₂mim]Cl for 30 minutes at 100° C. to yield 54.6 g of HMF and 3.7 g of fructose. In the second trial, fructose was reacted with 12-TPA at 100° C. for 45 minutes to yield 45.4 g of HMF and 19.4 g of fructose.

CONCLUSION

Although the foregoing embodiments have been described in some detail for purposes of clarity of understanding, it will be apparent that certain changes and modifications may be practiced within the scope of the appended claims. It should be noted that there are many alternative ways of implementing the processes of the present embodiments. Accordingly, the present embodiments are to be considered as illustrative and not restrictive, and the embodiments are not to be limited to the details given herein.

The invention claimed is:

1. A method of processing glucose, the method comprising:
   enzymatically converting glucose to fructose to yield a reaction mixture comprising the glucose and the fructose; and
   after the enzymatic conversion, converting up to all of the fructose in the reaction mixture to 5-hydroxymethyl furfural by introducing a choline-containing ionic liquid to the reaction mixture.

2. The method of claim 1, wherein enzymatically converting glucose to fructose further comprises introducing glucose isomerase and a borate salt or boric acid to glucose.

3. The method of claim 2, wherein the borate salt or boric acid is boric acid.

4. The method of claim 1, further comprising introducing an acid catalyst.

5. The method of claim 4, wherein the acid catalyst is selected from the group consisting of aluminum chloride, chromium(III) chloride, tin(IV) chloride, 12-MPA, and 12-TPA.

6. The method of claim 1, further comprising prior to enzymatically converting the glucose to the fructose, converting cellulose to the glucose via an acidolysis mechanism.

7. The method of claim 1, wherein the choline-containing ionic liquid is selected from the group consisting of choline acetate and choline salicylate.

8. The method of claim 1, wherein the glucose is provided in a stirred tank reactor.

* * * * *